(12) United States Patent
Guerret et al.

(10) Patent No.: US 9,714,212 B2
(45) Date of Patent: Jul. 25, 2017

(54) CHEMICAL COMPOUNDS DERIVED FROM NORMEMANTINE AND USE OF SAME IN THE MEDICAL FIELD

(71) Applicant: M2I DEVELOPMENT, Lacq (FR)

(72) Inventors: Olivier Guerret, Pern (FR); Samuel Dufour, Orthez (FR); Hafid Belhadj-Tahar, Toulouse (FR)

(73) Assignee: M2I DEVELOPMENT, Lacq (FR)

( * ) Notice: Subject to any disclaimer, the term of this patent is extended or adjusted under 35 U.S.C. 154(b) by 0 days.

(21) Appl. No.: 14/894,822

(22) PCT Filed: May 27, 2014

(86) PCT No.: PCT/EP2014/060981
§ 371 (c)(1),
(2) Date: Nov. 30, 2015

(87) PCT Pub. No.: WO2014/191424
PCT Pub. Date: Dec. 4, 2014

(65) Prior Publication Data
US 2016/0107982 A1 Apr. 21, 2016

(30) Foreign Application Priority Data
May 29, 2013 (FR) .................................. 13 01216

(51) Int. Cl.
| C07C 211/38 | (2006.01) |
| A61K 51/04 | (2006.01) |
| A61K 9/00 | (2006.01) |
| C07C 309/28 | (2006.01) |

(52) U.S. Cl.
CPC .......... C07C 211/38 (2013.01); A61K 9/0019 (2013.01); A61K 51/0455 (2013.01); C07C 309/28 (2013.01); C07C 2103/74 (2013.01)

(58) Field of Classification Search
CPC combination set(s) only.
See application file for complete search history.

(56) References Cited

PUBLICATIONS

Ikonomidou et al. "Why did NMDA receptor antagonists fail clinical trials for stroke and traumatic brain injury?" Lancet Neurology 2002, 1, 383-386.*
Ametamey et al., "Fluorine-18 Radiolabelling, Biodistribution Studies and Preliminary PET Evaluation of a New Memantine Derivative for Imaging the NMDA Receptor," Journal of Receptor and Signal Transduction Research, vol. 19, No. 1-4, 1999, pp. 129-141, XP008167695.
Ametamey et al., "PET Studies of $^{18}$F-memantine in Healthy Volunteers," Nuclear Medicine and Biology, Elsevier, vol. 29, No. 2, 2002, pp. 227-231.
French Preliminary Search Report, dated Feb. 27, 2014, for French Application No. 1301216.
International Search Report (Form PCT/ISA/210), dated Sep. 22, 2014, for International Application No. PCT/EP2014/060981.
Kotermanski et al., "Memantine Binding to a Superficial Site on NMDA Receptors Contributes to Partial Trapping," J. Physiol., vol. 587, No. 19, 2009 (published online Aug. 10, 2009), pp. 4589-4603.
Samnick et al., "Electrophysiological Study, Biodistribution in Mice, and Preliminary PET Evaluation in a Rhesus Monkey of 1-Amino-3-[$^{18}$F]fluoromethyl-5-methyl-adamantane ($^{18}$F-MEM): A Potential . . . Complex," Nuclear Medicine & Biology, vol. 25, No. 4, pp. 323-330, 1998, XP002720893.
Samnick et al., "Synthesis and Preliminary in Vitro Evaluation of a New Memantine Derivative 1-amino-3-[$^{18}$F]fluoromethyl-5-methyl-adamantane: A Potential Ligand . . . Complex," Journal of Labelled Compounds & Radiopharmaceuticals, vol. 39, No. 3, pp. 241-250, 1997, XP002720894.
Zdanys et al., "A Systematic Review of Off-Label Uses of Memantine for Psychiatric Disorders," Progress in Neuro-Psychopharmacology and Biological Psychiatry, Elsevier, vol. 32, No. 6, 2008 (available online Jan. 17, 2008), pp. 1362-1374.

* cited by examiner

*Primary Examiner* — Michael Barker
*Assistant Examiner* — Amanda L Aguirre
(74) *Attorney, Agent, or Firm* — Birch, Stewart, Kolasch & Birch, LLP

(57) ABSTRACT

The present invention concerns novel chemical compounds corresponding to formulae (I) and (II): (I) (II) which, when marked with fluorine-18, can be used as markers of NMDA receptors for carrying out studies with a scanner.

7 Claims, No Drawings

CHEMICAL COMPOUNDS DERIVED FROM NORMEMANTINE AND USE OF SAME IN THE MEDICAL FIELD

The present invention relates to novel chemical compounds derived from memantine and able to bind to N-methyl-D-aspartate (NMDA) receptors, which are activated by their bond with the neurotransmitter glutamate. An overactivation of NMDA receptors by glutamate is directly correlated with neurological diseases.

Due to the affinity of memantine derivatives for NMDA receptors, the invention also concerns labels for these receptors for use in medical imaging. The precursors of these derivatives are also objects of the invention.

It is known that NMDA receptors are involved in learning and memory (Nature, 319 (1986), p. 774-776). NMDA receptors are channels whose abnormal opening causes neurodegenerative disorders, for example Parkinson's disease, Alzheimer's disease or Huntington's disease. They are also implicated in neurological disorders such as epilepsy, hypoglycemia and perinatal ischemia, and in problems associated with head or spinal cord injuries, and in heart attacks. The action of NMDA receptor antagonists was thus investigated, but these antagonists often had undesirable side effects that precluded their consideration for possible use in a therapeutic treatment. It was noted that memantine is a noncompetitive NMDA receptor antagonist and that its side effects, at the therapeutic doses envisaged, were lesser than those of previously known antagonists (Neuropharmacology, Vol. 38(6), 15 Jun. 1999, p. 735-767).

NMDA receptors, unlike other ionotropic glutamate receptors, require for their activation a simultaneous binding of glutamate and a co-antagonist, glycine: it was thus sought to demonstrate a certain number of NMDA channel blockers by means of labeling with carbon-11 or fluorine-18 or iodine-123: the initial results were unsatisfactory because the radioligands were not specific or because the half-life of the radioelement selected was too short to permit a "production-injection-detection" protocol sufficiently short for an effective detection.

Among all the results, the best were obtained using $^{18}$F-memantine, which is an antagonist having an affinity for the NMDA receptor similar to that of memantine itself (see, for example, S. Samnick, S. Ametamey, M. Gold, P. Schubiger, Journal of Labelled Compounds and Radiopharmaceuticals, Vol. 29, no. 3, p. 241-250; Samnick S., Ametamey S., Gold M. R., Schubiger P. A., J. Lab. Comp. Radiopharm., 39, 241-250 (1997) or the same authors in Nucl Med Biol., May 1998; 25(4):323-30). The labeled blocker, when bound to the receptor, was detected with a positron emission tomography (PET) scanner (Nuclear Medicine and Biology 29 (2002), p. 227-231).

It thus proved that the use of $^{18}$F-memantine could be envisaged in the study of various neurological diseases, but nevertheless a certain number of side effects remain (in particular headaches, dizziness, sleepiness, hallucinations) which preclude recommending memantine generally (Progress in Neuro-Psychopharmacology and Biological Psychiatry, 32 (2008), p. 1362-1374). In fact, memantine has lesser side effects than the known NMDA receptor channel blockers, such as ketamine, due to the fact that the blocking mechanism is not the same: ketamine remains immobilized in the NMDA receptor when the antagonist disappears, whereas for memantine there is only partial residual trapping (J. Physiol. 587, 19(2009), p. 4589-4603).

It thus appears that the various NMDA receptor antagonists do not act in just one way, such that the advantages and the disadvantages of one antagonist are not necessarily found for another antagonist, and this is true even if the structures are similar.

For example, with the aim of maximizing the radiolabeling of NMDA receptors, it is important that the label, once injected, concentrates in the brain rather than in the other organs (lung, kidney, liver). For example, $^{18}$F-fluoromemantine has a distribution of 3.6% ID/g in the brain 60 minutes post-injection with a brain/blood ratio that increases over time: 2.40, 5.10, 6.33, and 9.27 at 5, 30, 60, and 120 minutes. This yield is rather low, and therefore finding derivatives that enable a higher concentration in the brain remains an issue in the study of NMDA receptors.

With the aim of maximizing the efficacy of NMDA receptor tracing, it is thus important to find novel labeled molecules characterized in that they are attainable with good yield on a schedule compatible with the half-life of $^{18}$F, and having both a good affinity for NMDA receptors and a sufficient affinity for the brain relative to the blood and the other organs.

According to the invention, the Applicant discovered a novel memantine derivative comprising an $^{18}$F atom that is easily attainable from a precursor and having a good affinity for the brain and a good affinity for NMDA receptors—different from those of the compounds of the literature cited above.

These differences can be exploited for the labeling of NMDA receptors and the visualization thereof via PET scans in order to study these receptors and their reaction to drug treatments or in the development of neurodegenerative diseases.

The first object of the present invention is thus a novel chemical compound corresponding to the formula (I), also called 2-fluoroethyl normemantine:

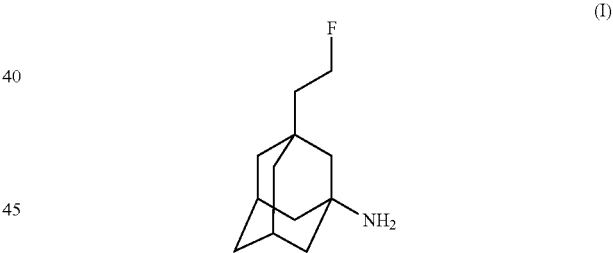

The molecule (I) can be in equilibrium with a protonated form of formula (II):

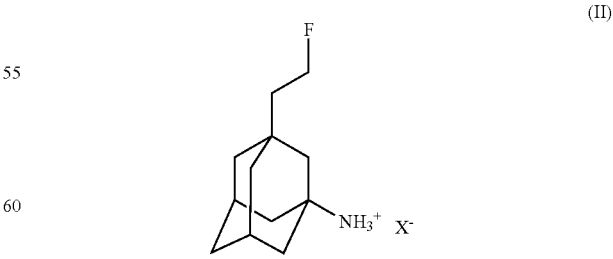

formula wherein X$^-$ indicates a counteranion from the biological environment or selected from the ions chloride, bromide, iodide, acetate, methane sulphonate, benzene sulphonate, camphosulphonate, tartrate, dibenzoate, ascorbate, fumarate, citrate, phosphate, salicylate, oxalate, bromohydrate, tosylate. The product of formula (II) is thus a salt of the product of formula (I).

The invention also concerns both precursors of the molecules (I) and (II). The first compound is the compound (P1) of formula:

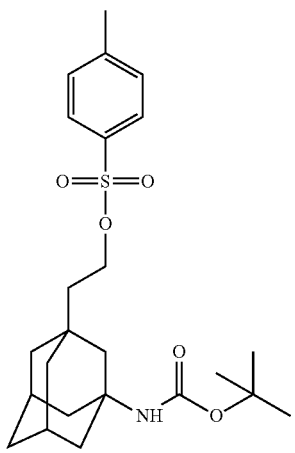

(P1)

The second compound is the compound (P2) of formula:

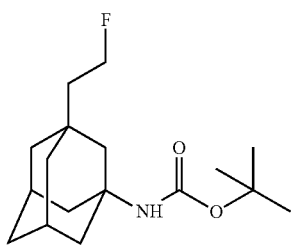

(P2)

The invention also concerns the use of the compound (I) or (II), wherein the fluorine atom indicated in the formula is preferably an $^{18}F$ atom, characterized in that an aqueous solution of one of these derivatives, or of a mixture thereof, is injected into the circulatory system of a living subject in order to detect the NMDA receptors of said subject by means of a positron emission scan to locate the $^{18}F$ atoms of the compound (I) or (II) and to study their behavior in studies of psychiatric disorders.

In a particular embodiment, the present invention concerns an aqueous solution of the compound (I) or of the compound (II), in particular an aqueous solution to be injected intravenously. The invention also concerns the use of the compounds (I), (II), (P1) or (P2) in drug compositions intended for the treatment of neurological diseases The present invention also concerns the use of an aqueous solution of the compound (I) or of the compound (II) for injection in a mammal in order to carry out a positron emission scan to locate the $^{18}F$ atoms in order to study the behavior of NMDA receptors during the study of neurological diseases.

The invention also concerns the compound (I) or the compound (II) for use as a drug.

Example 1

METHOD FOR PREPARING 3-AMINO-1-ADAMANTANE ETHANOL (B)

The starting product used is the hydrochloride of formula (A):

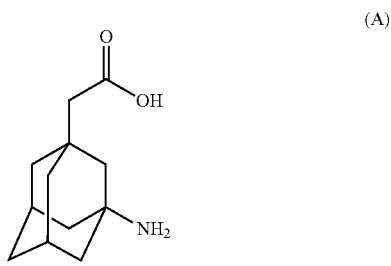 [SMILES: NC12CC3CC(C1)CC(CC(=O)O)(C3)C2]

(A)

which is a product marketed by the company Alinda under item number HLS0044-025.

In a 50 ml three-neck round-bottom flask, 338 mg of the product (A) (1.38 mmol) is suspended in 22 ml of anhydrous tetrahydrofuran, in an argon atmosphere. The flask is equipped with a condenser and a thermometer; the suspension is cooled to 0° C. Next, 0.66 ml of $BH_3SMe_2$ (6.9 mmol) is added dropwise: the reaction is highly exothermic and the reactor is cooled so as to maintain the reaction medium below 5° C. The addition is carried out over 30 minutes, low-temperature stirring is maintained for 8 hours, and then the temperature is allowed to return to room temperature for 8 hours. Heat is then applied to maintain the reaction medium at 50° C. for 16 hours in order to complete the binding reaction of the molecules (A) on borane-dimethyl-sulfide.

The medium is then cooled to 0° C. and the complex is hydrolyzed by slowly introducing 4.5 ml of methanol. Aqueous soda solution (10%) is then added to the reaction medium in order to obtain a pH above 10. Stirring is maintained for 1 hour and then the medium is concentrated to dryness at 40° C. under reduced pressure of 1 kPa.

The residue is then taken up in 6 ml of water which is then acidified by means of 33% hydrochloric acid solution until a pH of 1 is obtained. The aqueous phase is washed three times with 6 ml of methyl-tertiobutyl-ether. The aqueous solution is then brought to pH 10 by means of 30% sodium hydroxide solution. The product (B) is then collected by three extractions with 6 ml of dichloromethane. The fractions are combined and evaporated under reduced pressure of 1 kPa until a white solid is obtained (127 mg, yield: 47%).

The product is characterized by NMR:
$^1H$ NMR ($CDCl_3$, Bruker 400 MHz) 3.72 (2H, dt J=12 Hz, C$\underline{H}_2$OH), 2.8 (1H, OH), 2.21 (2H, broad, $NH_2$), 0.75-1.40 (14H, $CH_2$).

Example 2

PREPARATION OF N(3-ETHANOL ADAMANTANE)-O-TERTIOBUTYL CARBAMATE (C)

The product (B) obtained in example 1 is used as the starting product.

195 mg of the compound (B) is diluted in 1 ml of dioxane and 1 ml of water. 260 mg of sodium carbonate and then 400 mg of di-tert-butyl-dicarbonate in solution in 2 ml of dioxane are added. The medium is stirred for 72 hours.

10 ml of water is then added to the medium, the pH of which is adjusted to 3 by means of 1 N hydrochloric acid solution. The product is then extracted by successive extractions with 10 ml of ethyl acetate. The extractions are combined, dried over MgSO$_4$ and then the product (C) is collected by evaporation under reduced pressure of 1 kPa.

The product (C) is obtained in the form of a white solid (250 mg, yield 84%) and is characterized by NMR:
$^1$H NMR (CDCl$_3$, Bruker 300 MHz) 4.35 (1H, br, NH); 3.7 (2H, dt J=7 Hz, CH$_2$OH), 2.65 (1H, OH), 1.2-1.85 (29H, CH$_2$)

Example 3

PREPARATION OF N(3-(2-TOSYLATE-ETHYL) ADAMANTANE)-O-TERTIOBUTYL CARBAMATE (P1)

The product (C) obtained in example 2 is used as the starting product.

295 mg of compound C is diluted in 1 ml of dichloromethane. 200 mg of triethyl amine diluted in 1 ml of dichloromethane is then added. 200 mg of tosyl chloride diluted in 2 ml of dichloromethane is then added. The medium is stirred for 24 hours.

The medium is washed three times with 5 ml of water at acidic pH and then three times with 5 ml at pH 7. The organic phase is dried over MgSO$_4$ and then the product P1 is collected by evaporation under reduced pressure of 1 kPa.

The product (P1) is obtained in the form of a white solid (425 mg, yield 95%) and is characterized by NMR:
$^1$H NMR (CDCl$_3$, Bruker 300 MHz): 7.79 (2H, d, J=8.1 Hz, aromatic CH), 7.36 (2H, d, J=8.1 Hz, 2 aromatic CH), 4.34 (1H, broad, NH), 4.1 (2H, dt J=7.8 Hz, CH$_2$OH), 2.46 (3H, CH$_3$ tosyl), 2.08 (2H, m, CH$_2$CH$_2$OH), 1.81 (4H, m, CH$_2$CN), 1.63 (2H, CH$_2$), 1.55 (6H, CH$_2$), 1.4-1.43 (9H, CH$_3$).

Example 4

PREPARATION OF N(3-(2-FLUORO-ETHYL) ADAMANTANE)-O-TERTIOBUTYL CARBAMATE (P2)

The product (P1) obtained in example 3 is used as the starting product.

In a 100 ml three-neck round-bottom flask equipped with a condenser and a thermometer, under an anhydrous argon atmosphere, 225 mg of the compound (P1) (0.5 mmol) is dissolved in 30 ml of dichloroethane dried beforehand over P$_2$O$_5$.

The temperature of the reaction medium is lowered to −42° C. to avoid the strong exothermicity of the reaction.

1 mmol (13 μl) of (diethyl-amino)-sulfur trifluoride (hereafter "DAST") is then introduced into the flask dropwise. The medium is maintained at −42° C. for 2 hours and then the temperature is allowed to return to room temperature. After 16 hours under these conditions the temperature is lowered to −78° C. and the reagents are slowly hydrolyzed with aqueous potassium carbonate solution (3.5 g of K$_2$CO$_3$ in 12 ml of water; 25 mmol). After 2 hours the reaction is allowed to return to room temperature.

After one hour under these conditions the organic phase is collected, washed twice with water at pH 7, dried over magnesium sulfate and then concentrated under reduced pressure to obtain a pale yellow oil (66 mg, 45%).

The product is characterized by NMR as being the compound (P2):
$^1$H NMR (CDCl$_3$, Bruker 300 MHz): 4.50 (2H, dt J=7.8 Hz and J=43 Hz, CH$_2$F), 4.38 (1H, broad, NH), 1.95-1.43 (25H, CH$_3$).

Example 5

PREPARATION OF 1-AMINO-3-FLUORO-ETHYL-ADAMANTANE HYDROCHLORIDE (II) AND 1-AMINO-3-FLUOROETHYL-ADAMANTANE (I)

The following procedure is carried out starting with the compound obtained in example 4.

In a 50 ml round-bottom flask, 100 mg of the compound (P2) is solubilized in 3 ml of dichloromethane. The temperature of the medium is lowered to 0° C. and then 10 ml of hydrochloric ethyl ether is added.

After 8 hours at room temperature, 10 ml of 10$^{-3}$ M hydrochloric acid solution is added. The aqueous phase is collected and this extraction is repeated twice.

The fractions are combined and concentrated under vacuum. The oil obtained (55 mg) is taken up in 1 ml of water and the product is precipitated by adding 1 ml of ethanol. The precipitate, which is recovered via filtration (50 mg, 75%), is the compound (II) (characterized by mass spectrometry, M+=197.1567 C$_{12}$H$_{20}$FN (calculated 197.158); m/z (Cl—) 196.15 (M−1), 181.1 (M-NH$_2$), 150.1 (M-C$_2$H$_4$F).

The compound (II) is transformed into the compound (I) according to the following protocol.

50 mg of the compound (II) is diluted in 3 ml of water. The pH of the solution is brought to 9 by means of 10% sodium hydroxide solution. Extraction is carried out with 6 ml of dichloromethane, and the extraction is repeated twice. The fractions are combined and dried over magnesium sulfate. The solvent is evaporated under vacuum and the compound (I) is collected in the form of a pale yellow oil characterized by NMR:
$^1$H NMR (CDCl$_3$, Brüker 400 MHz): 4.54 (2H, dt J=12 Hz and J=48 Hz, CH$_2$F), 2.15 (2H, broad, NH$_2$), 1.65-1.26 (16H, CH$_3$).

For the following examples the term fluoroethyl normemantine will be used as a generic term to refer to the compound I or to its chloride salt II. The reason for this choice is that the salt II is used to produce injectable solutions whereas the molecule located in the cell extracts is the neutral hydrophobic molecule.

Example 6

PROPERTIES OF $^{18}$F-FLUOROETHYL NORMEMANTINE MAKING IT SUITABLE FOR LABELING NMDA RECEPTORS IN MEDICAL IMAGING

Toxicity

The objective of this test is to assess, qualitatively and quantitatively, possible toxic phenomena and the delay before onset thereof after a single administration of a predetermined dose of 0.125 μg/kg of body weight (which would correspond to more than 10$^4$ times the dose administered to humans). The tests were carried out on 5 male mice and the results were compared with those of 3 control mice receiving only 0.2 ml of 0.9% NaCl solution. All the mice are the species C57/Black 6J provided by Charles River Laboratories (France) and about 8 weeks old. The average weight of the mice at the beginning of the tests is about 32 g after an acclimation period of 2 weeks. The animals are housed three per cage (31 cm×46 cm×19 cm) at a temperature of 25° C.±2° C.

A 20 µg/l stock solution of $^{18}$F-fluoroethyl normemantine was prepared and then distributed in sterile 15 ml bottles. The volume administered to each mouse is defined as 0.125 µg/kg and is administered once intravenously by means of a suitable syringe and needle.

The animals are observed regularly the day of administration (after 30 minutes, 1 hour, 2 hours, 3 hours and 4 hours), and then once each day for at least 14 days. All the observations were unremarkable. After 14 days all the animals were euthanized and autopsied: no pathological change was noted.

These tests lead to the conclusion that $^{18}$F-fluoroethyl normemantine is not toxic at the doses tested. As these doses are much higher than those envisaged for labeling NMDA receptors, this product will be well tolerated for this application.

Example 7

PHYSICOCHEMICAL CHARACTERISTICS OF $^{18}$F-FLUOROETHYL NORMEMANTINE

Solubility in water superior to 100 mM, which is favorable for an injectable.

Lipophilicity: determined by $\log(P)=\log([I]_{n\text{-}octanol}/[I]_{water})$, by placing the compound (I) in a 50/50 mixture by volume of pH 7.4 buffer solution and octanol, separating the phases, then assaying by means of HPLC the level of the compound (I) present in each of said phases. One finds log(P)=3.1 (±0.5), which shows the Lipophilicity of I. This value is favorable to penetration in the brain.

Example 8

MOUSE STUDY OF DISTRIBUTION IN THE BODY

The tests were carried out on 3 batches of male mice and the results were compared with those of 3 control mice receiving only 0.2 ml of 0.9% NaCl solution. All the mice are the species C57/Black 6J provided by Charles River Laboratories (France) and about 8 weeks old.

A 20 µg/l stock solution of $^{18}$F-fluoroethyl normemantine was prepared and then distributed in sterile 15 ml bottles. The volume administered to each mouse is defined as 0.125 µg/kg and is administered once intravenously by means of a suitable syringe and needle.

At the prescribed time the mice are sacrificed, ground material from the organs is extracted and the concentration therein is analyzed by HPLC-MS assays.

The following results are obtained when sacrificing at 3 minutes
Sacrifice at 3 minutes:
  Brain: 12% of the injected dose
  Kidneys: 18%
  Liver: 20%
Sacrifice at 30 and 60 minutes:
  Brain/blood ratio (60 minutes): 6.015

One notes, with respect to the prior art, that fluoroethyl normemantine has a strong affinity for the brain (here, fluoromemantine was measured at 3% instead of 12%) and that the brain/blood ratio is comparable.

This experiment shows that the structural difference between memantine and the F-fluoroethyl normemantine compound leads to a different distribution behavior in the organs.

Example 9

RELATIVE AFFINITY OF $^{18}$F-FLUOROETHYL NORMEMANTINE FOR NMDA RECEPTORS

In this example, the affinity of fluoroethyl normemantine for NMDA receptors will be compared with that of glutamate (Glu) and of the product Dizocilpine (called "MK-801"), which are known NMDA receptor antagonists (see Neuroscience Letters, Vol. 80 (1), p. 111-114). MK-801 binds to two different sites in rat brain (Brain Res. 378, p. 133).

To that end, a material containing NMDA receptors will first be immersed in a solution containing labeled MK-801 (first experiment) or glutamate (second experiment) and then these materials are incubated in solutions containing fluoroethyl normemantine at various concentrations. Next, the radioactive emissions before and after this second incubation are compared. Lower emissions mean that fluoroethyl normemantine has a stronger affinity for NMDA receptors than that of the references and that NMDA receptors are inhibited thereby.

By means of these measurements, a correlation can be established between the concentration of the compound IE and NMDA receptor inhibition. The magnitude of the half-maximal inhibitory concentration ($IC_{50}$) is deduced therefrom.

First Experiment:

The compound MK-801 is thus used as an antagonist (product R0). As the product to be tested (product R1), either memantine or compound I is used. The experimental protocol is as follows: a homogenate of cerebral cortex membrane (140 µg of proteins) is prepared and then incubated for 2 hours at 37° C. with 10 nM [$^3$H]phencyclidine (tritiated MK-801) in the absence or presence of compound R1 (in buffer containing 5 mM HEPES/Tris (pH=7.4) and 0.1 mM ethyleneglycol tetraacetic acid). The comparison is made with an incubation of 10 mM MK-801. The samples are quickly filtered under vacuum through glass-fiber filters and rinsed with 50 mM iced Tris-HCl. The filters are dried and their radioactivity is counted on a scintillation counter. The concentration of compound R1 varies, and by comparing for each concentration the difference in emission between the control filter (MK-801 alone) and the MK-801/R1 mixture filter, the ratio of inhibition of compound R1 for each concentration is obtained. The result of this study is summarized in the following table I:

TABLE I

| R0 | R1 | [R1] Mol/l | Emission ratio 1st test (%) | Emission ratio 1st test (%) | Mean | IC$_{50}$ (Mol/l) |
|---|---|---|---|---|---|---|
| MK-801 | Memantine | $1 \cdot 10^{-9}$ | 97.8 | 95.5 | 96.9 | $1.1 \cdot 10^{-6}$ |
|  |  | $3 \cdot 10^{-9}$ | 111.5 | 95 | 103.3 |  |
|  |  | $1 \cdot 10^{-8}$ | 105.5 | 97.3 | 101.4 |  |
|  |  | $3 \cdot 10^{-8}$ | 98.5 | 96.5 | 97.5 |  |
|  |  | $1 \cdot 10^{-7}$ | 86.2 | 91.4 | 88.8 |  |
|  |  | $3 \cdot 10^{-7}$ | 77.1 | 69.2 | 73.1 |  |
|  |  | $1 \cdot 10^{-6}$ | 54.8 | 49.8 | 52.3 |  |
|  |  | $3 \cdot 10^{-6}$ | 27.9 | 30.1 | 29.0 |  |
|  |  | $1 \cdot 10^{-5}$ | 12.2 | 9.3 | 10.8 |  |
|  | Fluoroethyl normemantine | $1 \cdot 10^{-9}$ | 107.3 | 98.9 | 103.1 | $6.1 \cdot 10^{-6}$ |
|  |  | $3 \cdot 10^{-9}$ | 102.1 | 98.8 | 100.5 |  |
|  |  | $1 \cdot 10^{-8}$ | 98.4 | 107.7 | 103.1 |  |
|  |  | $3 \cdot 10^{-8}$ | 107.4 | 102.1 | 104.8 |  |
|  |  | $1 \cdot 10^{-7}$ | 92.5 | 98.6 | 95.5 |  |
|  |  | $3 \cdot 10^{-7}$ | 92.2 | 88.9 | 90.5 |  |
|  |  | $1 \cdot 10^{-6}$ | 79.4 | 91.8 | 85.6 |  |
|  |  | $3 \cdot 10^{-6}$ | 58.2 | 68.4 | 63.3 |  |
|  |  | $1 \cdot 10^{-5}$ | 42.9 | 41.5 | 42.2 |  |

From this measurement it is seen that fluoroethyl normemantine is an NMDA receptor inhibitor since it displaces MK-801. Its affinity is of an order of magnitude comparable with that of memantine ($10^{-6}$ M). When fluoroethyl normemantine is functionalized by a fluorine-18 atom it will thus be able, by binding to free NMDA receptors, to make it possible to locate said receptors using a positron emission scanner. It can thus be imagined that if one wished to study the effect of a novel drug on these receptors, the receptors remaining free in the presence of the novel drug could be mapped.

Second Experiment:

The experimental protocol is much the same as in the first experiment: a homogenate of cerebral cortex membrane (140 µg of protein) is prepared and then incubated for 1 hour at 4° C. with 5 nM tritiated glutamate (tritiated Glu) in the absence or presence of fluoroethyl normemantine (in buffer containing 5 mM Tris-HCl (pH=7.7) and 10 mM ethyleneglycol tetraacetic acid). The comparison is made with an incubation comprising 100 mM tritiated L-Glu. Following the incubation, the samples are quickly filtered under vacuum through glass-fiber filters and rinsed with 50 mM iced Tris-HCl. The filters are dried and their radioactivity is counted on a scintillation counter. The concentration of compound R1 varies, and by comparing for each concentration the difference in emission between the control filter (MK-801 alone) and the MK-801/R1 mixture filter, the ratio of inhibition of compound R1 for each concentration is obtained. The result of this study is summarized in the following table II:

TABLE II

| R0 | R1 | [R1] (M) | Emission ratio 1st test (%) | Emission ratio 1st test (%) | Mean |
|---|---|---|---|---|---|
| Glu | Fluoroethyl-normemantine | $1 \cdot 10^{-9}$ | 106.4 | 88.8 | 97.6 |
|  |  | $3 \cdot 10^{-9}$ | 101.9 | 101.6 | 101.8 |
|  |  | $1 \cdot 10^{-8}$ | 92.3 | 105.7 | 99.0 |
|  |  | $3 \cdot 10^{-8}$ | 108.0 | 91.0 | 99.5 |
|  |  | $1 \cdot 10^{-7}$ | 108.4 | 111.0 | 109.7 |
|  |  | $3 \cdot 10^{-7}$ | 94.2 | 109.0 | 101.6 |
|  |  | $1 \cdot 10^{-6}$ | 105.3 | 100.2 | 102.8 |
|  |  | $3 \cdot 10^{-6}$ | 104.3 | 92.5 | 98.4 |
|  |  | $1 \cdot 10^{-5}$ | 95.4 | 108.6 | 102.0 |

These results show that Glu is a better inhibitor than fluoroethyl normemantine. In this case, therefore, IC$_{50}$ cannot be measured.

These two experiments show that fluoroethyl normemantine has an affinity for NMDA receptors that would make it possible to use a fluorine-18 labeled derivative of fluoroethyl normemantine for imaging by positron emission scanning. Its ability to displace inhibitors such as MK-801 while being unable to displace Glu makes it possible to target the use of this compound for analyzing the mechanisms of action of drugs on psychiatric disorders such as Alzheimer's disease, schizophrenia, Parkinson's disease or others by PET scan, for example.

The invention claimed is:

1. A chemical compound of formula (I):

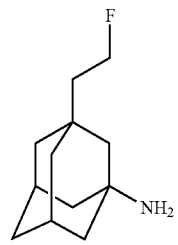 [SMILES: NC12CC3CC(C1)CC(CCF)(C3)C2]

or a salt thereof of formula (II):

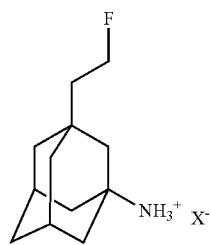

wherein X⁻ indicates a counteranion from a biological environment or selected from the ions chloride, bromide, iodide, acetate, methane sulphonate, benzene sulphonate, camphosulphonate, tartrate, dibenzoate, ascorbate, fumarate, citrate, phosphate, salicylate, oxalate, bromohydrate, or tosylate.

2. The compound according to claim 1, wherein the fluorine atom is a fluorine-18 ($^{18}F$) atom.

3. An aqueous solution of at least one compound of claim 1 which can be injected intravenously.

4. The compound of formula P2

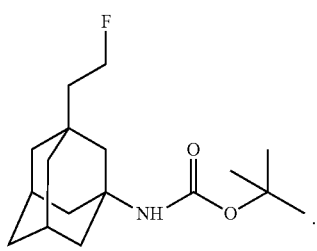
(P2)

5. The compound of formula P1 as a precursor of the compound P2

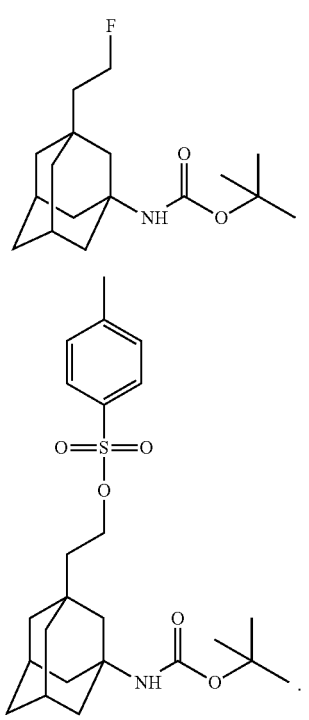

6. A method for the evaluation of the behaviour of NMDA receptors during the study of neurological diseases in a mammal which comprises injecting said mammal with a compound according to claim 1 or 2 and carrying out a positron emission scanner to locate the $^{18}F$ atoms.

7. A method for treating a neurological disease selected from Alzheimer's disease, schizophrenia, Parkinson's disease, Huntington's disease, epilepsy and perinatal ischemia, in a subject in need thereof comprising the administration of at least one compound selected from the group consisting of compounds (I), (II), (P1) or (P2) to the said subject

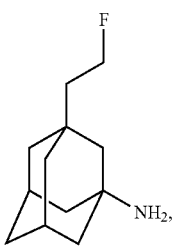
(I)

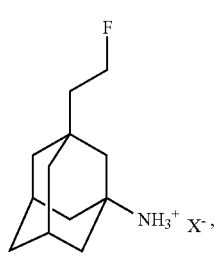
(II)

formula wherein $X^-$ indicates a counteranion from the biological environment or selected from the ions chloride, bromide, iodide, acetate, methane sulphonate, benzene sulphonate, camphosulphonate, tartrate, dibenzoate, ascorbate, fumarate, citrate, phosphate, salicylate, oxalate, bromohydrate, tosylate,

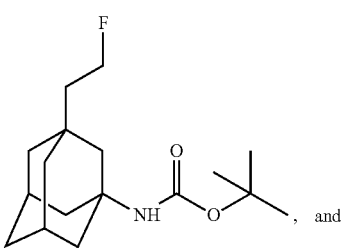
(P2)
, and

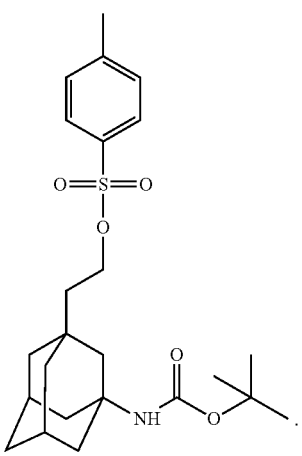
(P1)

* * * * *